United States Patent [19]

Das

[11] Patent Number: 5,869,048
[45] Date of Patent: *Feb. 9, 1999

[54] METHOD OF TREATING ULCERATIVE COLITIS WITH A MONOCLONAL ANTIBODY

[75] Inventor: Kiron M. Das, Martinsville, N.J.

[73] Assignee: University of Medicine & Dentistry, Newark, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 630,541

[22] Filed: Apr. 10, 1996

Related U.S. Application Data

[63] Continuation-in-part of Ser. No. 437,474, May 9, 1995, abandoned.

[51] Int. Cl.$^6$ .................................................. A61K 39/395

[52] U.S. Cl. ..................................... 424/141.1; 424/130.1

[58] Field of Search ............................... 424/130.1, 141.1

[56] References Cited

PUBLICATIONS

Nandiwada et al. (Apr. 1993). Gastroenterol. 104:A754.

*Primary Examiner*—Sheela Huff
*Attorney, Agent, or Firm*—Richard R. Muccino

[57] ABSTRACT

The present invention pertains to a method for treating ulcerative colitis in a human which comprises orally or rectally administering to the human a therapeutically effective amount of an antibody which binds to a colonic antigen associated with ulcerative colitis. In another embodiment, the present invention pertains to a method for treating ulcerative colitis in a human which comprises the steps of (a) obtaining from a human a colon epithelial cell extract containing a colonic antigen associated with ulcerative colitis; (b) purifying the colonic antigen until the antigen is substantially homogeneous; (c) developing an antibody which binds to the colonic antigen; (d) orally or rectally administering to a human having ulcerative colitis a therapeutically effective amount of the antibody to bind to the colonic antigen associated with ulcerative colitis. In yet another embodiment, the present invention pertains to a method for vaccinating a human against ulcerative colitis which comprises orally administering to the human a therapeutically effective amount of a colonic antigen associated with ulcerative colitis.

4 Claims, No Drawings

METHOD OF TREATING ULCERATIVE COLITIS WITH A MONOCLONAL ANTIBODY

This application is a continuation-in-part of parent application Ser. No. 08/437,474, filed May 9, 1995, now abandoned.

BACKGROUND OF THE INVENTION

1. Field of the Invention

This invention pertains to a method for treating ulcerative colitis. Specifically, the method comprises orally or rectally administering to a human having ulcerative colitis a therapeutically effective amount of an antibody which binds to a colonic antigen associated with ulcerative colitis.

2. Description of the Background

Ulcerative colitis is an idiopathic form of inflammatory bowel disease which manifests itself as a chronic, recurrent, nonspecific ulceration in the colon, chiefly of the mucosa. Ulcerative colitis is evidenced clinically by cramping, abdominal pain, rectal bleeding, and bloody diarrhea. Complications include bleeding, toxic megacolon, perforation of the colon, and carcinoma.

The disease usually begins in the rectosigmoid area and may extend proximally, eventually involving the entire colon, or it may attack most of the large bowel at once. Pathologic change begins with degeneration of the colonic epithelium and progressive infiltration of the lamina propria with plasma cells, eosinophils, lymphocytes, mast cells, and polymorphonuclear leukocytes. Crypt abscesses, epithelial necrosis, and mucosal ulceration are commonly found.

Although there is a familial tendency, the etiology of ulcerative colitis remains undefined, however, there is considerable evidence pointing towards autoimmunity. Acute and chronic inflammation within the colonic mucosa are known to generate inflammatory mediators which perpetuate the inflammatory process.

Current therapy for ulcerative colitis remains empirical and consists of treatment with sulfasalazine, glucocorticosteroids, and immunosuppressants. These agents require continuous administration to prevent recurrent inflammation once an acute episode has subsided. In recent years, 5-ASA compounds have been used with reduction in side effects but without much change in response rate as compared to conventional therapy.

The presence of a 40 KDa (Mr 40K, p40) colonic autoantigen and the circulating antibodies reactive against this protein have been detected in idiopathic ulcerative colitis (Takahasi et al., *J. Clin. Invest.* 76:311,1985) and in cotton top tamarins with spontaneous colitis (Das et al., *Gut* 33:48, 1992). Using hybridoma technology, a monoclonal antibody ($7E_{12}H_{12}$, IgM isotype) was developed against the epithelial antigen associated with ulcerative colitis (Das et al., *J. Immunol.* 139:77, 1987). The monoclonal antibody $7E_{12}H_{12}$ binds specifically to colonocytes along baso-lateral and brush border areas and it does not react with any other parts of the gastrointestinal tract including the small intestine. This colon epithelial specific protein (CSP) is localized in the cell membrane. Three recent studies demonstrated that $7E_{12}H_{12}$ reactive protein (CSP) indeed is recognized by a disease specific (ulcerative colitis) autoantibody of IgG1 subclass (Halstensen et al., *Gut* 34:650, 1993; Dasgupta et al., *Gut* 35:1712–1717, 1994; Hassan et al., *Clin. Exp. Immunol.*, 1995, 100:1457–1462).

Using an animal model of colitis, researchers have recently shown that the $7E_{12}H_{12}$ monoclonal antibody given by enema provides beneficial effect against the Dextran Sulfate Sodium induced murine colitis (Nandiwada et al., *Gastroenterology* 104:A754, 1993). The study involved intracolonic administration of $7E_{12}H_{12}$ prior to and along with Dextran Sulfate Sodium and the results suggested that the $7E_{12}H_{12}$ monoclonal antibody is significantly effective in improving the clinical and histological integrity of the colonic mucosa.

Autoimmunity has been implicated in the pathogenesis of ulcerative colitis (UC) since its initial report 36 years ago demonstrating the presence of circulating antibody in ulcerative colitis against colonic antigen (Perlman, P., *J. Exp. Med.* 1959;110:657–673). Subsequently, other investigators reported the presence of various serum antibodies occurring in up to 70% of patients with ulcerative colitis directed against intestinal goblet cells (Brandtzaeg, P., *Gastroenterology* 1995;109:307312; Hibi et al., *Clinical Exp. Immunol.* 1983, 54, 163–168) as well as directed against colonic epithelial brush border, suggesting the multiplicity of antigenic cellular proteins. Tissue bound IgG eluted from ulcerative colitis colon but not from non-ulcerative colitis diseased colon, has been shown to react with an Mr 40K colonic protein (p40). The ulcerative colitis colon eluted IgG (CCA-IgG) also reacted with the autologous p40. Lamina propria lymphocytes from ulcerative colitis also secrete IgG reactive to the mucosal extract enriched in p40. Subsequently, a partial sequence study indicated that p40 belonged to a tropomyosin family.

Using highly enriched p40, a murine monoclonal antibody (mAb), termed $7E_{12}H_{12}$ (IgM isotype) was developed (Das, K. M. et al., *J. Immunol.* 1987;139:77–84). Immunocytochemical studies using the $7E_{12}H_{12}$ monoclonal antibody demonstrated specific recognition of the colonic epithelial cells and not with 13 other epithelial organs including other parts of the gastrointestinal tract and small intestinal enterocytes. The reactivity was predominantly localized at the plasma membrane in the apical (brush border area) and basolaceral domains of colonocytes (Das, K. M. et al., *J. Immunol.* 1987;139:77–84). Using two and three color immunofluorescence assay (Halstensen, T. S. et al., *Gut* 1993;34:650–657), the $7E_{12}H_{12}$ reactive epitope was also localized exclusively in colonic enterocytes, but not in small intestinal enterocytes, with increasing intensity caudally, expanding to intense cytoplasmic expression in the rectum. Furthermore, IgG1 antibody and activated complement products, C3b and terminal complement complex, were co-localized with $7E_{12}H_{12}$ epitope on the colonic epithelium in ulcerative colitis but not in Crohn's disease (Halstensen, T. S. et al., *Gut* 1992;33:902–908), suggesting a specific antibody response against the $7E_{12}H_{12}$ reactive protein and perhaps followed by activation of complement system. This in situ observation of a specific IgG1 autoantibody response against the $7E_{12}H_{12}$-reactive protein was confirmed using sera from a large number of patients with ulcerative colitis and other disease controls (Dasgupta et al., *Gut* 35:1712–1717). Sera from patients with primary sclerosing cholangitis also contain specific autoantibody against the $7E_{12}H_{12}$-reactive protein that is shared by colon and biliary epithelial cells (Mandal, A. et al., *Gastroenterology* 1994; 106:185–192). Indeed, following systematic screening of 17 various epithelial organs using the $7E_{12}H_{12}$ monoclonal antibody, epitope(s) cross-reactive to colonocytes were localized only in the epidermis, biliary epithelium, non-pigmented epithelial cells of the ciliary processes in the eye, and chondrocytes of joints (Das, K. M. et al., *Gastroenterology* 1990;98;464–469; Bhagat et al., *Gastroenterology* 1994;107;103–108), the extracolonic organs most commonly involved in ulcerative colitis. These findings from several independent studies provide evidence suggesting that an autoimmune response to the $7E_{12}H_{12}$-reactive protein is an important immunopathological event in ulcerative colitis.

SUMMARY OF THE INVENTION

The present invention pertains to a method for treating ulcerative colitis in a human which comprises orally or rectally administering to the human a therapeutically effective amount of an antibody which binds to a colonic antigen associated with ulcerative colitis.

In another embodiment, the present invention pertains to a method for treating ulcerative colitis in a human which comprises the steps of:

(a) obtaining from a human a colon epithelial cell extract containing a colonic antigen associated with ulcerative colitis;

(b) purifying the colonic antigen until the antigen is substantially homogeneous;

(c) developing an antibody which binds to the colonic antigen;

(d) orally or rectally administering to a human having ulcerative colitis a therapeutically effective amount of the antibody to bind to the colonic antigen associated with ulcerative colitis.

In yet another embodiment, the present invention pertains to a method for vaccinating a human against ulcerative colitis which comprises orally administering to the human a therapeutically effective amount of a colonic antigen associated with ulcerative colitis.

DETAILED DESCRIPTION OF THE INVENTION

This invention pertains to a method for treating ulcerative colitis. Specifically, the method comprises orally or rectally administering to a human having ulcerative colitis a therapeutically effective amount of an antibody which binds to a colonic antigen associated with ulcerative colitis. The antibody may be administered in the form of an enema (local treatment) in patients with mild to moderate distal ulcerative colitis. The theoretical basis for the present invention is that the antibody will bind to the colon specific antigen (CSP) thus blocking the epithelial binding of circulating auto antibodies that has been shown to activate the complement cascade causing inflammation and mucosal destruction (Halstensen, et al., *Gut* 34:650–657, 1993).

Applicant has developed a monoclonal antibody (mAb), $7E_{12}H_{12}$ (IgM isotype), that specifically reacts with colon epithelium and not with small intestinal enterocytes and many other epithelial organs (*J. Immunology* 1987: 139;77). However, $7E_{12}H_{12}$ is reactive against extracolonic organs commonly involved in ulcerative colitis (UC) (*Gastroenterology* 1990;98:484; *Gastroenterology* 1994; 107:103). IgG1 autoantibody in ulcerative colitis colocalizes along with $7E_{12}H_{12}$ epitope (*Gut* 1993;34:650). This hybridoma was obtained following the immunization of Balb/c mice with a human colonic protein extract highly enriched for p40, a putative colonic autoantigen in ulcerative colitis. Applicant has also shown that p40 could be either a colon-specific isoform of tropomyosin (TM) or a tropomyosin related molecule (*J. Immunol.* 1993; 150:2487). To further delineate this relationship, we examined the reactivity of $7E_{12}H_{12}$ monoclonal antibody with various known isoforms of recombinant human tropomyosins (hTMs 1–5) derived from fibroblast using ELISA and immunotransblot analysis. None of these 5 isoforms reacted with $7E_{12}H_{12}$ monoclonal antibody. As determined by immunofluorescence and FACS analyses, $7E_{12}H_{12}$ monoclonal antibody reacts with several colon cancer cells, namely DLD-1, LS180, T84, but not with HT-29 and many other non-colonic epithelial cells (293-T, HeLA, pancreatic cancer) and hematopoietic cells (K562, KGI, Daudi). Immunoprecipitation with $7E_{12}H_{12}$ monoclonal antibody of $^{125}$I-labelled membrane proteins of DLD-1 revealed a consistent major band of 185 kDa, in addition to a minor band of the expected 40 kDa protein. DLD-1 cells grown with gamma interferon (10 μg/ml) increased the 185 kDa protein by 3 fold, indicating its amplification by the cytokine. To purify the $7E_{12}H_{12}$-reactive protein, a membrane enriched fraction (MEF) of DLD-1 cells was used. The membrane enriched fraction was isolated by the standard methods, solubilized in detergents, and subjected to affinity chromatography using purified $7E_{12}H_{12}$-IgM. Again, the predominant protein reactive to $7E_{12}H_{12}$ was 185 kDa protein. The protein was purified to homogeneity by electroelution following SDS-PAGE. In addition, we have determined that this protein binds to various lectins, suggesting that it is a glycoprotein.

A strong association exists between primary sclerosing cholangitis (PSC) and ulcerative colitis (UC). As set out above, we earlier developed a monoclonal antibody (mAb), $7E_{12}H_{12}$, that specifically reacts with normal colon epithelial cells and biliary epithelial cells as shown by immunocytochemistry (*Gastroenterology* 1990;98:464). An autoimmune response in primary sclerosing cholangitis was also demonstrated against this unknown cross-reactive protein (*Gastroenterology* 1994;106:185). To further characterize the shared immunoreactive protein, we have utilized a cholangioearcinoma cell line (CCC), and several colon cancer cell lines (DLD-1, LS180, T-84 & HT-29) and non-colonic epithelial cells (293-T). Cells were examined by immunofluorescence assay and FACS analysis. The immunoreactive protein was identified by immunoprecipitation with $7E_{12}H_{12}$ monoclonal antibody, using surface labeled ($^{125}$I-Na) cell extracts from CCC & DLD-I cells. Immunotransblot analysis was performed using membrane enriched fractions (MEF) of all the positive cell lines. Membrane enriched fractions were obtained using the standard methods. Immunofluorescence and FACS analysis demonstrated $7E_{12}H_{12}$ reactivity restricted to CCC, DLD-1, LS180, T-84 but not with HT-29, and 293 T cells. Immunoprecipitation demonstrated the reactive protein of 185 kDa in CCC and DLD-I cells. The 185 kDa protein binds with several lectins, suggesting that it is a glycoprotein (gp185). Immunotransblot analysis using membrane enriched fraction also demonstrated gp185 to be clearly present in CCC, DLD-I, LS 180 and T84 cells, but not in HT-29 and 293T cell extracts. Using several monoclonal and polyclonal antibodies to carcinoembryonic antigen (CEA), we further determined that gp185 does not belong to the known biliary glycoprotein (BGP) of the CEA family. These studies demonstrate a unique membrane associated glycoprotein (gp185) shared by colon and biliary epithelial cells.

The tropomyosins (TMs) are a large group of closely related actin-binding proteins present in all eukaryotic cells. These proteins are critical in the regulation of cytoskeletal structure and various functions related to cell motility. Eight distinct tropomyosin isoforms have been identified in human fibroblast cells. Classically, tropomyosins are known to be intracellular proteins and in the intestine they have been localized at the rootlet of brush border of microvilli by immunocytochemical staining. In experimental colitis and in patients with ulcerative colitis (UC), autoantibodies against tropomyosins have been demonstrated (*J. Immunol.* 1993; 150:2487). To elucidate how the autoantibody against this intracellular protein could be involved in the pathogenesis of ulcerative colitis, we have examined the presence of various isoforms of human tropomyosin (hTM) on the surface of the colonic epithelial cells and colon cancer cell lines. Isoform specific monoclonal antibodies (mAb) such as CGI (hTM1), CGβ6 (hTM2 and hTM3), CG3 (hTM5), were utilized for FACS analysis. Colon cancer cell lines included HT-29, DLD-I, LS180, T-84 and non-colon cell line was 293T. Cells were incubated with various antibodies on ice in PBS containing 0.1% sodium azide and 1% BSA, followed by appropriate FITC-conjugated antibodies. Cells were fixed in 1% formaldehyde and analyzed by FACS. Only one monoclonal antibody, CG3, (anti-hTM5) showed clear and strong reaction on the surface of the colonic epithelial cells, T84 and LS 180, and less strong on DLD-1. No reactivity was seen with HT-29 and 293 T cells. None of the other antibodies, including unrelated isotype control monoclonal antibodies reacted with any of the cell lines by FACS. These data indicate that a certain tropomyosin isoform (e.g., hTM5 or related protein) is expressed on the surface of the colon epithelial cells.

We have further examined isoforms of human tropomyosins (hTMs) in isolated colonic epithelial cells from operative specimens of colon from patients with colon cancer, (normal segments), ulcerative colitis and Crohn's disease (CD). Human tropomyosin isoform specific monoclonal antibodies and recombinant human tropomyosins were utilized to examine the immunoreactivity by ELISA and by quantitative immunotransblot analysis. Local autoantibody responses against various recombinant human tropomyosin isoforms were examined by using lamina propria lymphocytes (LPL) isolated from colon from ulcerative colitis (n=19), Crohn's disease (n=12), and non-IBD controls (n=17). These included 40 operative specimens and 8 colonoscopic biopsy specimens. Lamina propria lymphocytes were grown in vitro for 10 days and IgG synthesized in vitro was used in the ELISA against recombinant human tropomyosin 1, 2, 3, and 5 isoforms. The major hTM isoforms present in colonic epithelial cells belong to hTM 4 and 5, and smaller amounts of hTM 1,2 and 3, with quantitative differences among normal, ulcerative colitis and Crohn's disease. The immunoreactivity of the IgG synthesized in vitro by lamina propria lymphocytes from ulcerative colitis was significantly higher against hTM5 ($p<0.03$) and hTM 1 ($p<0.02$), but not with hTM2 & hTM3, when compared with the IgG synthesized by lamina propria lymphocytes from Crohn's disease and non IBD. 12 of 19 ulcerative colitis reacted with hTM1 & hTM5. However, none of the 12 Crohn's disease, 17 non-IBD, and 7/19 ulcerative colitis reacted with any of the hTM isoforms. These studies define hTM isoforms in colonic epithelial cells and demonstrate the production of human tropomyosin-isoform specific autoantibody by mucosal lymphocytes in two-thirds of patients with ulcerative colitis and not in Crohn's disease and non-IBD controls.

The colonic antigen associated with ulcerative colitis used in the present invention may be any colonic antigen associated with ulcerative colitis. Preferably, the colonic antigen is reactive to monoclonal antibody $7E_{12}H_{12}$, $7E_{12}H_{12}$ reactive protein. More preferably, the colonic antigen is p40 colonic autoantigen or gp185 colonic autoantigen. Most preferably, the colonic antigen is gp185 colonic autoantigen. The gp185 colonic autoantigen may be responsible for the transport of hTM from intracellular compartments to the cell membrane thus allowing the hTM5 or hTM5 component with gp185 to be recognized by the immune effect for cells in ulcerative colitis.

The antibody which binds to a colonic antigen associated with ulcerative colitis used in the present invention may be any antibody. Preferably, the antibody is a murine antibody or a humanized antibody directed against gp185 or specific for an epitope of hTM5 that is expressed on the surface of colon epithelium. More preferably, the antibody is the monoclonal antibody $7E_{12}H_{12}$.

The amount of antibody which binds to a colonic antigen associated with ulcerative colitis used in the present invention is a therapeutically effective amount. A therapeutically effective amount of antibody is that amount of antibody necessary to bind to a colonic antigen associated with ulcerative colitis blocking the epithelial binding of circulating and/or local auto antibodies causing ulcerative colitis. The exact amount of antibody is a matter of preference subject to such factors as the type of condition being treated as well as the dosage recommended or permitted for the particular antibody. In general, the amount of antibody agent employed is the dosage required to obtain the desired result. In a preferred embodiment, the dosage of $7E_{12}H_{12}$ mouse antibodies in an enema for patients with ulcerative colitis will be in the range from about 50 μg/day to about 500 μg/day, preferably from about 100 μg/day to about 400 μg/day, and more preferably from about 150 μg/day to about 300 μg/day. Most preferably, the dosage of $7E_{12}H_{12}$ will be about 100 μg in the form of a retention enema given once or twice a day for up to about 8 weeks.

The present invention extends to methods for preparing the antibodies which bind to a colonic antigen associated with ulcerative colitis used in the present invention. The antibodies may be developed using standard techniques and apparatus known to those skilled in the art. In a preferred embodiment, the invention is directed to a method for treating ulcerative colitis in a human which comprises the steps of:

(a) obtaining from a human a colon epithelial cell extract containing a colonic antigen associated with ulcerative colitis;

(b) purifying the colonic antigen until the antigen is substantially homogeneous;

(c) developing an antibody which binds to the colonic antigen;

(d) orally or rectally administering to a human having ulcerative colitis a therapeutically effective amount of the antibody to bind to the colonic antigen associated with ulcerative colitis.

In a preferred embodiment, the substantially homogeneous colonic antigen in step (b) is amplified by DNA recombinant technology prior to developing an antibody which binds to the colonic antigen in step (c).

The present invention extends to methods for vaccinating a human against ulcerative colitis. The method comprises orally administering to the human a therapeutically effective amount of a colonic antigen, or a part thereof, associated with ulcerative colitis. Preferably, the colonic antigen, or a part thereof, is administered initially in small doses followed by larger doses to desensitise the patient to the colonic antigen.

The antibodies of the present invention may be used together with pharmaceutically acceptable carriers to provide pharmaceutical compositions which can be administered to a human orally or rectally, or both, in amounts effective to provide a variety of therapeutic activity. Of course, the type of carrier will vary depending upon the mode of administration desired for the pharmaceutical composition as is conventional in the art as well as the desired site of action, e.g.,. Preferably, the antibody is administered orally or rectally to the human.

The present invention is further illustrated by the following examples which are not intended to limit the effective scope of the claims. All parts and percentages in the examples and throughout the specification and claims are by weight of the final composition unless otherwise specified.

EXAMPLES

These examples illustrate the development of the monoclonal antibody $7E_{12}H_{12}$ which binds to the colonic autoantigen associated with ulcerative colitis, and the effectiveness of $7E_{12}H_{12}$ in the treatment of distal ulcerative colitis.

Production of Monoclonal Antibody $7E_{12}H_{12}$

In order to produce the $7E_{12}H_{12}$ monoclonal antibody of this invention, six-week old BALB/c mice were immunized with an emulsion of 100 pg of a highly enriched Mr 40K protein (1 mg/ml) in an equal volume of complete Freund's adjuvant, given subcutaneously over the neck, in the footpad and intraperitoneally. The Mr 40K protein was purified from human colons. In order to produce the Mr 40K protein, human colon specimens were obtained within one-half hour of surgery for colectomy and stored in negative $-80°$ C. The colon extracts were normal segments which were removed from patients with colon cancer. The colon tissue was then thawed on ice and after removal of fats, the tissue was suspended in 50 ml of a buffer A containing 50 mM Tris HCl pH 8.0, 0.15M NaCl, 2 mM EDTA, 2 mM PMSF and a cocktail of protease inhibitors comprised of Aprotinine 0.3 $\mu$M, Pepstatin 1 pM, and Leupeptine 1 pM. The colon tissue was minced with a fine scissor and centrifuged at 2,000 g for 10 minutes, and the supernatant was discarded. The step was repeated at least 7 times until the supernatant was clear.

Next, 100 ml of buffer B (which is the same as buffer A, except that it contained 10 mM EDTA) was added to the final precipitate, and the precipitate was left on ice for half an hour and then homogenized over ice using a POLYTRON™ for 5 minutes using 15 second bursts interspersed with one minute intervals. The homogenate was then centrifuged at 10,000 g for 30 minutes. The supernatant was removed and ultracentrifuged at 100,000 g for 90 minutes. Next, the supernatant was frozen and thawed 3 times and centrifuged for 10 minutes at 10,000 g to remove the precipitate. The supernatant was dialyzed against a buffer C containing 20 mM Bis-Tris Propane, pH 6.5 at $4°$ C.

Next, an ion exchange chromatography was performed using a DEAE column. The dialyzed material was delipidated by mixing it with an equal volume of 1,1,2-trichlorotrifluoroethane, vortexed and centrifuged at 2,000 g×30 minutes. The top aqueous layer was separated, filtered through 0.22 micron syringe filter and used for chromatography. Five mg of sample was loaded and the column was washed with buffer C until O.D. 280 absorption became steady near zero. Then the column was eluted with step gradient of 0.2M, 0.35M, and 0.48M NaCl in buffer C. Peaks were monitored by O.D. at 280 nm. The peaks were collected separately and dialyzed against a buffer D containing 20 mM phosphate and 0.15M NaCl, pH 7.4.

Hydrophobic Interaction Chromatography was then performed using the 0.35M and 0.48M NaCl eluates from the ion-exchange column. A 1×10 cm econo column (Bio-Rad) was packed with 5 ml bed volume of phenyl sepharose and equilibrated with 20 mM phosphate, 0.15M NaCl, pH 7.4 containing 0.8M ammonium sulfate. The protein sample was adjusted to 0.8M ammonium sulfate by addition of solid ammonium sulfate and loaded to the column as 1 mg of protein per ml of bed volume. The column was washed with loading buffer until the O.D. 280 steady near zero. Then, the column was eluted stepwise with 20 mM phosphate, 0. 15M NaCl, pH 7.4 and then with distilled water.

Next, immunotransblot analysis was performed. Eluted proteins were subject to a 10% SDS polyacrylamide gel electrophoresis and electrophoretically transferred to nitrocellulose paper. The nitrocellulose strips were washed, dried and exposed for autoradiography at $-80°$ C.

After immunizing the mice with the highly enriched Mr 40K protein emulsion, the mice were given 40 $\mu$g of highly purified Mr 40K protein intraveneously one day prior to fusion. The splenic lymphocytes were mixed with cells of non-secretor BALB/c-derived myeloma line (NSO) in the mid-logarithmic phase of growth in a ratio of 8:1 spleen to myeloma cells. Fusion was performed with a 50% polyethylene glycol (mol. wt. 4,000; Merck, Darmstadt, West Germany) using standard techniques.

After fusion, cells were washed once with HAT medium (100 pM hypoxanthine, 400 nM-aminopterin, 16 pM-thymidine 20% fetal calf serum, 10% NCTC109, 1% penicillin and streptomycin, 1% non-essential amino acids in DME) and gently resuspended at $5×10^5$ myeloma cells/ml.

Cultures were set up with 100 $\mu$l of the suspension per well of 96-well flat-bottom plates (Linbro, Flow Laboratories Inc. McLean, Va.). Cultures were maintained at $37°$ C. in 8% $CO_2$ and screening for antibodies was performed on day 14 by an ELISA. Clonal growth was assessed by inspection. Positive clones were expanded in 24 well flat-bottom microculture plates (Linbro, Flow Laboratories, Inc., McLean, Va.) and cloned in soft agar. Expanded clones were maintained in vitro in 25 $cm^2$ flasks (Corning Glass Works, Corning, N.Y.) or injected intraperitoneally into 2, 6, 10, 14 tetramethylpentadecane (Pristane; Aldrich Chemical Co., Milwaukee, Wis.)—primed BALB/c mice for the production of ascitic fluid. Aliquots of expanded clones were also frozen and stored in liquid nitrogen without subsequent loss of secretory capacity.

Of the monoclonal antibodies produced, the monoclonal antibody designated $7E_{12}H_{12}$ gave the highest reactivity in the ELISA. The monoclonal antibody $7E_{12}H_{12}$ was further purified by subcloning. The hybridoma secreting monoclonal antibody $7E_{12}H_{12}$ is on deposit with the American Type Culture Collection, Rockville, Md., where it was received Apr. 16, 1987 and catalogued as ATCC #HB9397.

Effectiveness of $7E_{12}H_{12}$ in the Treatment of Distal Ulcerative Colitis

To determine the effectiveness of the monoclonal antibody $7E_{12}H_{12}$ in the treatment of distal ulcerative colitis, a non-randomized open label trial of $7E_{12}H_{12}$ monoclonal antibody was conducted for 8 weeks.

The design of the study was as follows:
Screening
1. History
2. Physical examination
3. Baseline clinical lab investigations CBC, Chem 21 (including albumin), U/A sedrate
4. Flexible sigmoidoscopy
Day 14
1. History 2. Physical examination
3. Overall global status
Day 28
1. History
2. Physical examination
3. Flexible sigmoidoscopy
4. Clinical lab tests
Day 56 and Day 84
1. History
2. Physical examination
3. Flexible sigmoidoscopy
4. Clinical lab tests Study Procedures 1. Medical history—This included a history of when the patient was first diagnosed with ulcerative colitis, a history of medications received, whether or not these medications were successful in treating the disease, and especially the documentation of the diagnosis of ulcerative colitis, the duration of the patient's most recent episode of active colitis, and the treatment used to induce remission. The extent of disease during the most recent episode of disease activity will be documented.

2. Assessment of symptoms—The severity of symptoms was assessed using the disease activity index (DAI) which was a sum of numerical scores grading the severity of symptoms. These include character of stool, presence of blood in stool, endoscopic appearance, and overall status (general well being).

3. Height and weight

4. Vital signs

5. Complete physical examination

6. Clinical laboratory tests—Blood and urine samples were obtained for CBC, sed rate, Chem-21. LFT's and UA.

7. Pregnancy test—Urine or serum HcG pregnancy test in females of childbearing potential.

8. Endoscopic examination—Flexible endoscopy was performed on initial screening and graded according to the severity index discussed earlier and biopsies were taken at 15 cm from anal verge and the highest point of inflammation. The procedure was repeated at Day 28 and Day 56 by the same endoscopist.

9. Biopsy—Specimens obtained were evaluated by the same pathologist.

Management of Adverse Events

Throughout the duration of the study, the investigator closely monitored each patient for any evidence of intolerance, or the development of clinical or laboratory evidence of adverse effect. All adverse events which occurred during the course of the study were reported in detail and followed to a satisfactory resolution. The description of the adverse event included the time of onset, duration, severity, etiology, the relationship of adverse events to the study drug and any treatment required. The investigator rated the severity of any adverse event according to the following definitions:

Mild: The adverse event was transient and easily tolerated by the patient.

Moderate; The adverse event caused patient discomfort and interrupted the patient's usual activities.

Severe: The adverse event caused considerable interference with the patient's usual activities and may be incapacitating or life threatening.

The investigator used the following definitions to assess the possible relationship of the adverse event to the study drug.

Probable: The adverse event had a timely relationship to study drug administration and a potential alternative etiology was not apparent.

Possible: The adverse event had a timely relationship to study drug administration. However, a potential alternative etiology existed which may be responsible for the adverse event.

No Relationship: Definitive evidence existed that the adverse event is related to an etiology other than study drug.

Premature withdrawals—Each patient had the right to withdraw from the study at any time without prejudice. The investigator could discontinue any patient's participation when he felt it was necessary for any reason, including adverse event or failure to comply with protocol. Modification of protocol—The modification had to be documented in writing. Any change in research activity had to be reviewed and approved by the IRB prior to implementation.

Subject Informed Consent

Subjects were given the following information upon which to give an informed consent.

I have been informed that I have ulcerative colitis and understand that this treatment with the monoclonal antibody, called $7E_{12}H_{12}$, is an experimental treatment. Monoclonal antibodies are immunoglobulin proteins produced by B cells (part of immune system) in the mouse. The mouse is immunized with a specific protein and the mouse's B cells are extracted and then grown in tissue culture so that they can continue producing the antibodies against the specific protein. The antibodies can bind with the protein and block its destruction of tissue. The $7E_{12}H_{12}$ monoclonal antibody reacts specifically to the lining cells of the colon, called colonic epithelial cells. Initial experimental data in the laboratory suggest that the protein recognized by the $7E_{12}H_{12}$ monoclonal antibody may cause immune response in patients with ulcerative colitis.

Purpose of Procedure. The rationale of the current therapy is to block this protein by introducing the $7E_{12}H_{12}$ monoclonal antibody directly into the colon by enema. I understand that if included in the study, I will take the enema containing 100 μg of the murine monoclonal antibody called $7E_{12}H_{12}$ developed against a colon protein, once or twice a day for up to 8 weeks depending on my clinical condition. Doses may be increased to 250 μg by enema once or twice a day.

Table 1 outlines the clinical data on 3 patients who were treated with the monoclonal antibody $7E_{12}H_{12}$ via enema. In summary, 2 of 3 patients went into remission following treatment. The third patient did not improve.

TABLE 1

| Patient | DAI**** | Endoscopic Appearance | Treatment |
|---------|---------|----------------------|-----------|
| 1*      | 5/12    | 2/3                  | none, day zero |
|         | 0/12    | 0/3                  | 8 wks $7E_{12}H_{12}$, 100 μg/day |
|         | 5/12    | 2/3                  | 4 wks placebo |
|         | 0/12    | 0/3                  | 8 wks $7E_{12}H_{12}$, 100 μg/day |
| 2**     | 6/12    | 2/3                  | none, day zero |
|         | 4/12    | 1/3                  | 8 wks $7E_{12}H_{12}$, 100 μg/day |
|         | 0/12    | 0/3                  | 8 wks $7E_{12}H_{12}$, 200 μg/day |

TABLE 1-continued

| Patient | DAI**** | Endoscopic Appearance | Treatment |
|---------|---------|----------------------|-----------|
| 3*** | 6/12 | 2/3 | none, day zero |
|  | 6/12 | 2/3 | 4 wks $7E_{12}H_{12}$, 100 µg/day |

*Patient no. 1 received 20 weeks of therapy; 8 weeks of treatment with $7E_{12}H_{12}$/enema 100 µg/day (disease free); 4 weeks of treatment with a placebo (disease reoccurred); 8 weeks of treatment with $7E_{12}H_{12}$/enema 100 µg/day (disease free).
**Patient no. 2 received 16 weeks of therapy; 8 weeks of treatment with $7E_{12}H_{12}$/enema 100 µg/day (partial response); 8 weeks of treatment with $7E_{12}H_{12}$/enema 200 µg/day (disease free).
***Patient no. 3 received 4 weeks of therapy with $7E_{12}H_{12}$/enema 100 µg/day without any response. Patient no. 3 decided to discontinue further treatment with the antibody.
****Disease Activity Index (DAI) included the Endoscopy Appearance score in addition to clinical symptoms and signs.

Immunoreactivity of $7E_{12}H_{12}$ Monoclonal Antibody Against Recombinant Human Tropomyosin Isoforms Since studies using 2 proteolytic peptides of p40 demonstrated that p40 belongs to tropomyosin family, the reactivity of $7E_{12}H_{12}$ monoclonal antibody was examined against all the available tropomyosin isoforms. Recombinant human tropomyosin isoforms (hTM1, 2, 3, 4, & 5) were developed from human fibroblast 3 5 and obtained from Dr. Jim Lin, University of Iowa. Each of the isoforms was used to coat the ELISA plate (150 nanogram/well) in triplicate and the binding of the protein was examined by using isoform specific monoclonal antibodies. hTM isoform coated wells were sequentially incubated with $7E_{12}H_{12}$ monoclonal antibody (1 µ/well), alkaline phosphatase conjugated anti-mouse IgM (µ chain specific), followed by the substrate p-nitrophenyl phosphate and the color was read, at 405 nm. An unrelated mouse IgM (MOPC-IgM) was used as control.

The reactivity of $7E_{12}H_{12}$ monoclonal antibody was also examined by immunotransblot analysis using chemiluminescence method described below. Anti-TM antibodies were used in parallel as positive controls.

Identification and Purification of the $7E_{12}H_{12}$-reactive Protein

Immunoprecipitation using surface labeled DLD-1 cells
Preparation of DLD-1 cell membrane fraction
Ion exchange chromatography
Immunotransblot analysis
Immunoaffinity chromatography
Lectin binding property of gp185
Analysis of gp185
Immunoelectronmicroscopic localization of gp185:

Non-reactivity of $7E_{12}H_{12}$ Monoclonal Antibody Against TMs

In both ELISA and transblot studies, $7E_{12}H_{12}$ monoclonal antibody did not react with any of the TM isoforms, hTM1–5 although anti-TM antibodies consistently reacted with respective TM isoforms.

$7E_{12}H_{12}$-Reactive Protein Detected by Immunotransblot Analysis

Using purified $7E_{12}H_{12}$-IgM and transblot analysis using chemiluminescence method, the major immunoreactive protein in the DLD-1 cell membrane extract was consistently detected at a high molecular weight of Mr 185K and not at p40 area (Figure not shown). This was also confirmed by immunoprecipitation of $^{125}$I-Na labeled DLD-1 cells described below.

Interestingly, $7E_{12}H_{12}$-reactive protein (Mr 185K) and colonic tropomyosins (TMs) (Mr 32K to Mr 42K) (Das, K. M. et al., Journal of Immunology 1993;147:215–221) are co-purified and indeed DLD-1 cell extract as well as colonic mucosal extract highly enriched in colonic TMs reacts with the $7E_{12}H_{12}$ monoclonal antibody as well as with anti-TM antibodies. The purification of tropomyosins by conventional biochemical procedures involving boiling, ultracentrifugation, hydrophobic-interaction chromatography, ion exchange chromatography also enriched the $7E_{12}H_{12}$-reactive protein as measured by the ELISA using the $7E_{12}H_{12}$ monoclonal antibody. Similarly, immunoaffinity purified protein(s) using $7E_{12}H_{12}$-IgM (described below) contained both Mr 185K protein as well as TMs.

Immunoprecipitation Using $^{125}$I-labeled DLD-1 Cell Membrane Proteins

Using DLD-1 colon cancer cells that react with $7E_{12}H_{12}$ monoclonal antibody (Das, K. M. et al., Cellular Immunology 1993;147:215–221; Das, K. M. et al., Clin. Exp. Immunol. 1992;88:138–142), we consistently observed the major single band at Mr 185K by careful immunoprecipitation of $^{125}$I-labeled membrane proteins with the $7E_{12}H_{12}$ monoclonal antibody (Figure not shown). Control epithelial cells such as HeLa, gastric cancer, and pancreatic cancer cells did not show any reactive protein, neither did several other colon cancer cells including HT-29 and Colo 205 (Figure not shown). Several hematopoietic cells including K562, KG1, Daudi and HL60 also did not react with $7E_{12}H_{12}$ monoclonal antibody. We further determined that the 185K protein is glycosylated and binds strongly with wheat germ lectin (WGA) and with con A (Figure not shown).

Immunoaffinity Chromatography

Using purified $7E_{12}H_{12}$-IgM covalently coupled with CNBr activated sepharose 4B, several proteins bound to the column as shown by protein staining. Immunotransblot analysis demonstrated clear reactivity at Mr 185k that was purified by electroelution following SDS-PAGE (Figure not shown).

Immunoelectronmicroscopy

Immunoelectronmicroscopy using the monoclonal antibody demonstrated membrane localization of the reactive protein at the apical and lateral membrane areas (Figure not shown).

In this study, we clearly demonstrate that the major immunoreactive protein recognized by the $7E_{12}H_{12}$ monoclonal antibody is a membrane associated glycoprotein with relative molecular mass being 185K or gp185 and not the p40 as we originally thought. Since $7E_{12}H_{12}$ monoclonal antibody was developed against the highly enriched p40 (Das, K. M. et al., J. Immunol. 1987;139:77–84), we considered this monoclonal antibody as an anti-p40 antibody. The weak immunotransblot reactivity seen at the Mr 40K area further supported our initial assumption, and the higher molecular weight protein seen at about Mr 200K area was initially considered by us as probably aggregated protein. However, current studies using isoform specific recombinant TMs (hTM1–5) and more sensitive methods, including chemiluminescence, immunoprecipitation, immunoaffinity chromatography, made clear that the major immunoreactive protein recognized by $7E_{12}H_{12}$ monoclonal antibody is a membrane associated glycoprotein with Mr 185K. From various immunobiochemical studies, including the affinity chromatography, as described here, it is apparent that both gp185 and p40 are co-purified during the extraction process. Tropomyosins are known to bind several proteins in vivo (Lees-Miller, J. P. et al., BioEssays 1991;13:429). It is possible that p40 related colonic tropomyosin binds in vivo with gp185 and forms a complex, or colonic tropomyosin binds to gp185 in vitro after the cells are lysed. Thus, gp185 was probably present as a minor contaminant complexing with the p40 that was used to develop the monoclonal antibody. However, specific autoantibody responses in ulcerative colitis are seen against both p40 as well as gp 185. Although the cross-reactivity, if any, between p40 and gp185 is currently unknown, it is also possible that the p-40-gp185 complex may act as a target for this autoimmune response. The immunoreactivity of $7E_{12}H_{12}$-reactive protein with autoantibody (predominantly IgG1 isotype) in ulcerative colitis was demonstrated in several independent studies using various methods. These included (Halstensen et al., Gut 1993;34:650–657) co-localization in-situ by 2 and 3 color immunofluorescence assay and with patients' sera against the enriched gp185 colon extract using antigen capture ELISA (Dasgupta et al., Gut 35:1712–1717, 1994) competitive inhibition using the colonic cancer cell line DLD-1 (Hassan et al., Clin. Exp. Immunol., 1995, 100:1457–1462). The disease specificity of this autoantibody reactivity was demonstrated in each of these studies using several disease controls and a large number of sera. The colon specificity of the $7E_{12}H_{12}$ reactive protein as shown in several earlier studies using immunoperoxidase methods and immunofluorescence assay ((Das, K. M. et al., J. Immunol. 1987;139:77–84); Halstensen, T. S. et al., Gut 1993;34:650–657) is further confirmed biochemically using various epithelial cell lines. It is interesting that not all colon cancer cell lines, e.g. DLD-1, LS180, and T-84 cells, express $7E_{12}H_{12}$ reactive protein but HT-29, colo-205, do not (Hassan et al., Clin. Exp. Immunol., 1995, 100:1457–1462). None of the non-colonic epithelial cell lines showed any reactivity in FACS, in immunotransblot analysis and immunoprecipitation experiments. However, the cholangiocarcinoma cell line demonstrated Mr 185K protein in the transblot analysis, supporting the previous immunocytochemical results demonstrating restricted extracolonic distributions matching with the extracolonic manifestations of ulcerative colitis.

Various anticolon antibodies reported with less-defined test systems, over the last 35 years, may be merely an epi-phenomenon, as also suggested in the Il-2 knock-out mice, or may depend on a certain genetic background.

Since 1962, when Perlmann and Broeberger initially described the possibility of antibody-dependent cellular cytotoxicity (ADCC) as a mechanism of cellular damage in ulcerative colitis (Perlman et al., International Symposium on Immunopathology, New York, Grune & Stratton, 1962;288–302), many studies confirmed these observations. Using DLD-1 cells (but not with HT-29), such ADCC with ulcerative colitis sera was demonstrated and evidence has been obtained that $7E_{12}H_{12}$ epitope is a target molecule in the ADCC, although other epithelial antigens may be involved as well. It is intriguing that gamma-interferon increases the vulnerability of the target cells for ADCC and this may be explained, in part, by cytokine mediated up-regulation of the $7E_{12}H_{12}$ reactive gp185 target in ADCC (Das, K. M. et al., *Journal of Immunology* 1993;147:215–221). The role of ADCC in the pathogenesis of human diseases is uncertain. However, the cellular destruction in ulcerative colitis may be contributed by activation of complement cascade by the IgG1 autoantibody directed to the membrane-associated gp185 that has an intriguing colonic epithelial expression having increasing intensity caudally with the maximum expression in the rectum.

Whereas expressions of major histocompatibility class II antigens on colon epithelium and bile duct epithelium have been shown in the presence of inflammations, such expression of the class II molecules on colon and bile duct epithelium in the context of specific epithelial autoantigen(s) such as gp185 may be an important target for autoimmune responses. Specific autoantibodies directed against gp185 present in both ulcerative colitis and PSC support this notion. Various cytokines released during this immune recognition may also influence the inflammatory process. Similar autoantigenic expression in the uveal tract and joints, along with class II molecule, may be important in the pathogenesis of these target organ-involvement.

While Mr 185K protein is identified in the colon and biliary epithelial cells, the cross-reactive protein(s) in keratinocytes, ciliary epithelium and chondrocytes is unknown. It is possible that gp185 belongs to a family of closely related proteins or multiple isoforms of the same protein with selective cellular expression. The immunologic response against the target molecules may be triggered by some local factors, e.g. trauma, or molecular mimicry against a bacterial or a viral peptide crossreactive to the membrane associated gp185. However, such a possible molecular mimicry is currently unknown. Extracolonic organs that are involved during active disease and improve following remission or colectomy may be due to specific crossreactive autoantibodies, whereas, some of the extracolonic organs involved in ulcerative colitis and not influenced by colonic disease, including total colectomy, such as PSC, may be primarily associated with specific antigen-primed autoreactive T-cell response. Further characterization of gp185 and immune responses against the specific peptide(s) in gp185 may provide important biochemical information to explain autoimmunity in ulcerative colitis as well as its extra-colonic manifestations.

It is especially advantageous to formulate the pharmaceutical compositions in dosage unit forms for ease of administration and uniformity of dosage. The term dosage unit forms as used herein refers to physically discrete units suitable for use as a unitary dosage, each unit containing a predetermined quantity of active ingredient calculated to produce the desired therapeutic effect in association with the pharmaceutical carrier.

Throughout this application, various publications have been referenced. The disclosures in these publications are incorporated herein by reference in order to more fully describe the state of the art.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A method for treating ulcerative colitis in a human which comprises rectally administering to the human a therapeutically effective amount of monoclonal antibody $7E_{12}H_{12}$, which is secreted by hybridoma ATCC HB9397, which binds to a colonic antigen associated with ulcerative colitis.

2. The method according to claim 1, wherein the antibody is administered in an amount from about 50 μg/day to about 500 μg/day.

3. The method according to claim 1, wherein the colonic antigen is p40.

4. The method according to claim 1, wherein the colonic antigen is gp185.

* * * * *